United States Patent
Bhuiyan

(10) Patent No.: US 11,941,809 B1
(45) Date of Patent: Mar. 26, 2024

(54) GLAUCOMA DETECTION AND EARLY DIAGNOSIS BY COMBINED MACHINE LEARNING BASED RISK SCORE GENERATION AND FEATURE OPTIMIZATION

(71) Applicant: iHealthScreen Inc., Queens Village, NY (US)

(72) Inventor: Alauddin Bhuiyan, Queens Village, NY (US)

(73) Assignee: HEALTHSCREEN INC., Queens Village, NY (US)

( * ) Notice: Subject to any disclaimer, the term of this patent is extended or adjusted under 35 U.S.C. 154(b) by 0 days.

(21) Appl. No.: 18/219,433

(22) Filed: Jul. 7, 2023

(51) Int. Cl.
  G06T 7/00 (2017.01)
  G16H 50/20 (2018.01)
  G16H 50/30 (2018.01)

(52) U.S. Cl.
  CPC ........... *G06T 7/0012* (2013.01); *G16H 50/20* (2018.01); *G16H 50/30* (2018.01); *G06T 2207/20081* (2013.01); *G06T 2207/20084* (2013.01); *G06T 2207/30041* (2013.01)

(58) Field of Classification Search
  None
  See application file for complete search history.

(56) References Cited

U.S. PATENT DOCUMENTS

| | | |
|---|---|---|
| 8,787,638 B2 * | 7/2014 | Zee .................... A61B 3/12 382/128 |
| 10,123,689 B2 | 11/2018 | Jia et al. |
| 10,963,737 B2 | 3/2021 | Odaibo et al. |
| 11,080,850 B2 | 8/2021 | Cho et al. |
| 2011/0190657 A1 * | 8/2011 | Zhou ................ G16H 50/70 600/558 |
| 2017/0169565 A1 | 6/2017 | Huang et al. |
| 2019/0191988 A1 | 6/2019 | Gargeya |
| 2021/0118525 A1 * | 4/2021 | Craig ................ G16B 20/20 |
| 2022/0165418 A1 * | 5/2022 | Li ................. G06V 10/7747 |
| 2022/0230300 A1 * | 7/2022 | Kawczynski ........ G06T 7/0004 |

FOREIGN PATENT DOCUMENTS

CN 113011450 * 6/2021

* cited by examiner

*Primary Examiner* — Nancy Bitar
(74) *Attorney, Agent, or Firm* — Carter, DeLuca & Farrell, LLP

(57) ABSTRACT

Systems, methods of and computer program products for predicting and detecting the onset of glaucoma are provided.

20 Claims, 6 Drawing Sheets

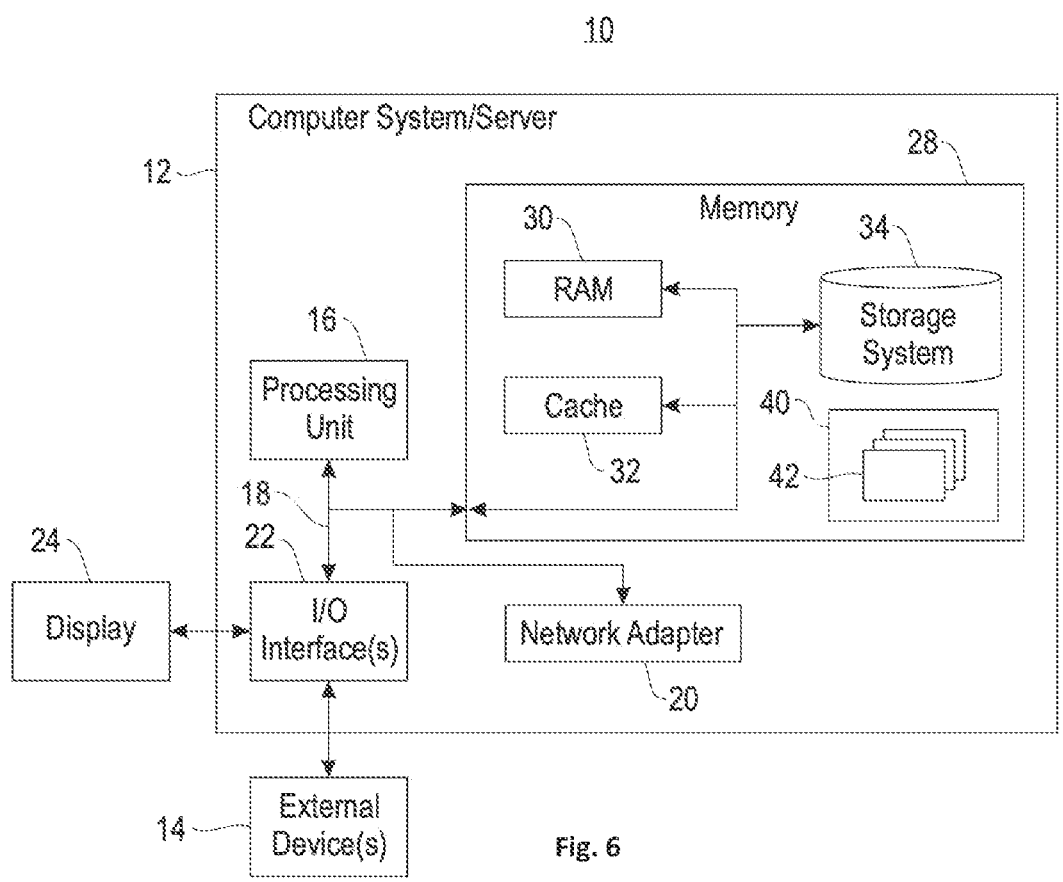

GLAUCOMA DETECTION AND EARLY DIAGNOSIS BY COMBINED MACHINE LEARNING BASED RISK SCORE GENERATION AND FEATURE OPTIMIZATION

BACKGROUND

Glaucoma is a group of eye conditions that damage the optic nerve, the health of which is vital for good vision. This damage is often caused by an abnormally high pressure in your eye. Although scientists are unsure as to what causes the most common types of glaucoma, it has been found that many people with glaucoma have high eye pressure. Therefore, treatments that lower eye pressure may help to slow the disease. There's no way to prevent glaucoma. An eye exam may be used in order to detect glaucoma before it affects an individual's vision, but current techniques are unable to accurately, efficiently, and reliably detect such glaucoma in individuals. Therefore, there is a need to have a technique that allows for the accurate, efficient, and reliable prediction and detection of the onset of glaucoma.

SUMMARY

According to some embodiments of the present disclosure, methods of and computer program products for predicting and detecting the onset of glaucoma are provided. In various embodiments, a method of detecting glaucoma is provided. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a system is provided including a computing node comprising a computer readable storage medium having program instructions embodied therewith. The program instructions are executable by a processor of the computing node to cause the processor to perform a method. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a computer program product for backing up and restoring a managed cluster of nodes is provided including a computer readable storage medium having program instructions embodied therewith. The program instructions are executable by a processor to cause the processor to perform a method. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a risk score may be generated for each of multiple indications of glaucoma, such as a cup-disc ratio, peripapillary atrophy, disc hemorrhage, blood vessel structure/fractal dimension, nasalness of blood vessels, and retinal entire image. Examples of cup-disc ratio may include binary cup-disc ratio as glaucoma vs. non-glaucoma, and a 3-class cup-disc ratio for glaucoma and non-glaucoma probability score. Detection of peripapillary atrophy may be achieved with a higher confidence using the Optimizing Small Datasets Problem—Domain-Specific Pre-Training (OSDP-DSPT) algorithm, described further below, as well as an independent peripapillary atrophy measure to determine a risk score associated with peripapillary atrophy. Disc hemorrhage may be assessed via the OSDP-DSPT algorithm as well as an independent disc hemorrhage measure. Each of the risk scores may be generated based on an output of a separate machine learning model, such as a deep learning model, a deep neural network, or the like, with the multiple indications as input to each of the the deep learning models. A classification model, such as a logistic model tree (LMT) may be used to combine each of the risk scores to produce a probability/likelihood risk score of glaucoma. This technique may achieve a substantially high accuracy for the detection of glaucoma.

In various embodiments, the technique described herein may break down a glaucoma screening task into multiple, such as three, individual problems in a type of divide and conquer approach. Each of the aforementioned models may learn the respective features that are relevant to glaucoma independent of other features. For example, the features may include glaucoma features such as peripapillary atrophy and disc hemorrhage versus fifteen different features of retinal pathologies such as drusen, hemorrhage, exudates, cotton wool spots, and the like. Such an approach may increase the accuracy of feature detection for whether glaucoma is or will be present.

In various embodiments, the techniques described herein may divide a main problem into subproblems, each of which is associated with a machine learning model that may be pre-trained and trained. The output of each machine learning model may be combined using a classification model, such as a LMT, which may output value(s) used to determine whether glaucoma is or will be present. In particular, the output of each model may be a prediction for a particular indication of glaucoma. The classification model may learn from predictions from the output of each model. The classification model may provide a probability/likelihood risk score of glaucoma. The risk score of glaucoma may act as a binary classifier, for example by comparing the risk score to a predetermined or dynamically set threshold. The threshold may be set in a way that is balanced and/or a clinically useful sensitivity and specificity.

In various embodiments, a glaucoma probability/likelihood risk score may be generated using a OSDP-DSPT algorithm and a disc hemorrhage model (DHM). In various embodiments, peripapillary atrophy may be detected using OSDP-DSPT and a peripapillary atrophy model and to generate the glaucoma probability/likelihood risk score.

In various embodiments, a disc nasalness based glaucoma probability/likelihood risk score may be generated using OSDP-DSPT and a retinal disc center 20 degree image. This may be combined with information regarding other indications of glaucoma which may be generated separately. In various embodiments. In various embodiments, a glaucoma probability/likelihood risk score may be generated from the vessel architecture, which may be analyzed by removing the disc area of a fundus image and considering the entire blood vessel structure.

BRIEF DESCRIPTION OF THE DRAWINGS

FIG. 6 depicts a computing node according to various embodiments of the present disclosure.

DETAILED DESCRIPTION

Figure 1:
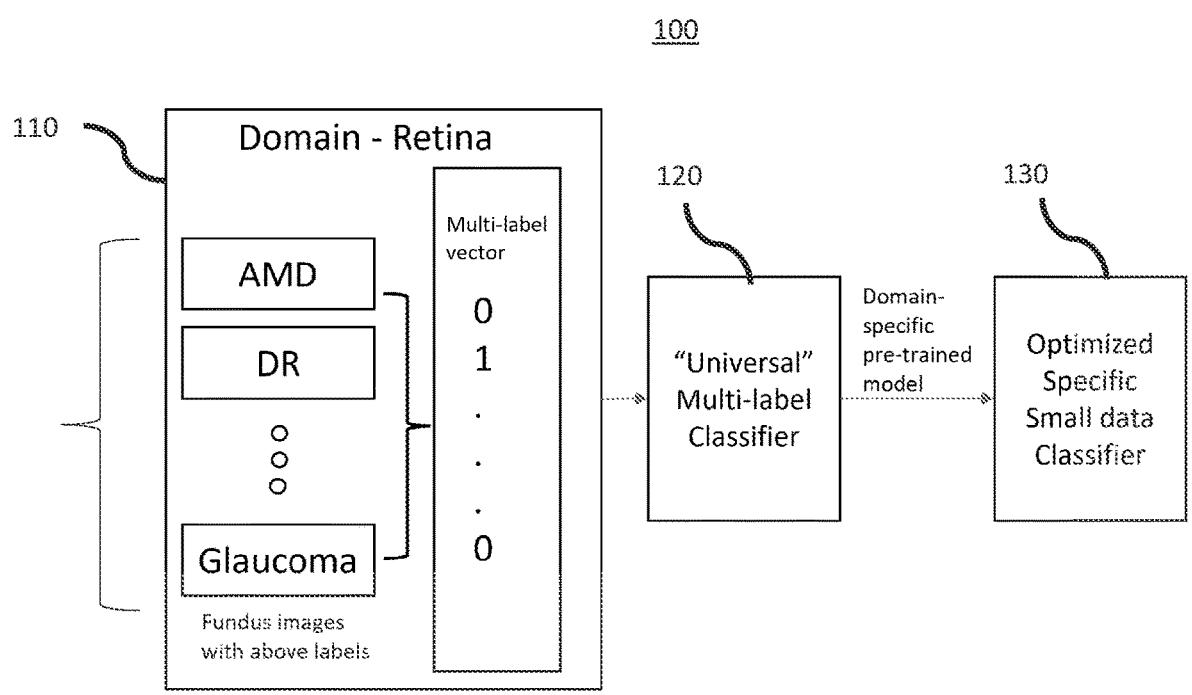
FIG. 1 depicts an overall high-level architecture of a proposed pre-training technique according to various embodiments of the present disclosure.

Glaucoma is a group of diseases that damage the eye's optic nerve and can result in vision loss and blindness. Glaucoma, with age-related macular degeneration (AMD) and diabetic retinopathy (DR), is one of the three leading causes of blindness in developed countries, and is now the second leading cause of blindness globally, after cataracts.

Glaucoma is characterized by loss of retinal ganglion cells (RGCs), which results in visual field impairment and structural changes to the retinal nerve fiber layer (RNFL) and optic disc. Glaucoma has few early symptoms. Over 3 million individuals in the United States have glaucoma, over 76 million individuals have glaucoma worldwide. It is projected that 111 million individuals will have glaucoma by the year 2040. About half of those affected do not know that they have glaucoma. In many cases, when glaucoma is detected, it is already too late, i.e., the case will involve an individual with irreversible visual field loss.

The social and economic costs of vision loss from glaucoma are very high. Early detection of conditions associated with glaucoma halts a downward spiral in overall health, which may be affect an individual because of the onset of: depression, loss of independence, need for nursing home care, falls, fractures, and death. These adverse outcomes are also extremely costly. The total economic burden of vision loss and blindness from all causes in the United States, including the direct and indirect costs, is now $145 billion, which is expected to triple by the year 2050 in real dollars, with increased longevity generally (Source: Prevent Blindness).

Therefore, there is a need to identify, at the early stages, individuals for treatment that have or that are suspected/prone to have glaucoma. Although glaucoma prediction/screening has been a focus area in medical research for many years, it is still difficult to diagnose, let alone predict, glaucoma with high degree of confidence. In particular, there is a lack of techniques or algorithms that present a more holistic approach in predicting and detecting or screening for the onset of glaucoma.

Recent studies have shown that retinal cup-disc ratio (CDR) may be highly correlated with glaucoma. The relationship between estimated RGC counts and CDR suggests that an assessment of change in CDR may be a sensitive method for the evaluation of progressive neural losses in glaucoma. Even relatively small changes in CDR may be associated with significant losses of RGCs, especially in eyes with larger CDRs, such as CDR>0.5. Enlarged CDR may be one indicator of the risk of glaucoma. Most individuals fall within an average vertical CDR of 0.4, and 2.5% of the population have a cup/disc ratio of over 0.7. In general, an eye with vertical CDR above 0.5 may be considered a glaucoma suspect and thus screening of the general population based on CDR may be highly effective for referral.

The medical imaging and diagnostics field has been revolutionized by advances in artificial intelligence (AI) and deep learning in recent years. Extensive research interest is being shown in using artificial intelligence for solving medical problems. For example, Ting et al. detailed the potential applications of AI in ophthalmology. Gulshan et al. showed the application of AI in diabetic retinopathy from fundus images using deep learning. There have been groundbreaking works published on late AMD prediction and diabetes screening in primary care settings. There is also considerable research in using deep learning in other medical areas such as multiple sclerosis, neurodegeneration and age-related macular degeneration.

Although several conventional AI techniques have been proposed to measure the cup-disc ratio, they have not been validated for screening individuals for glaucoma. Conventional research has focused on the detection of glaucoma, the disease itself, rather than the possible onset of glaucoma. For example, one conventional technique for glaucoma detection focused on using the standard Online Retinal fundus Image database for Glaucoma Analysis (ORIGA). This technique was proposed by Saxena et al. in 2020, which has a receiver operating characteristic (ROC) area under the curve (AUC) of 0.82.

Several of these studies with conventional techniques refer to glaucoma. To the extent that these studies refer to glaucoma, however, they do not differentiate the term glaucoma, a diagnosis of the disease that requires demonstrated structural and functional abnormalities, from glaucoma suspect, which is exactly what its name implies—a category or marker with an increased likelihood of disease that merits further investigation—i.e., a prediction of the onset of the disease. For example, in the ORIGA analysis described above, these terms are conflated, and the definition used for glaucoma, taken from ORIGA, is just C/D>0.65, which is purely structural, and which is inadequate for glaucoma diagnosis. Furthermore, the methodology in this ORIGA analysis is inadequate for deep learning, with only 90 images used for training. As another example, several of the other studies all have the stated goal of detecting glaucoma, by various means. However, this stated goal, by definition, would be too restrictive and not be appropriate for predicting, screening for, or detecting the onset of glaucoma.

Optimizing Small Datasets Problem—Glaucoma (Domain-Specific Pre-Training): OSDP-DSPT Algorithm The following describes the Optimizing Small Datasets Problem (OSDP) for Glaucoma, and more specifically the ODSP-Domain-Specific Pre-Training (DSPT) algorithm. Deep learning often requires an abundance of data. For example, in the medical field this data may include an abundance of medical images. However, the medical field, it may be rare to have such images to perform effective data science using traditional approaches. This is often the case for images of glaucoma-related abnormalities as well. For example, there is often a dearth of data available for disc hemorrhage, peripapillary atrophy and other lesions, and/or abnormalities. The novel techniques as described herein optimize machine learning techniques despite using small datasets. For example, such techniques described herein may be applied to glaucoma.

In various embodiments described herein, as much data as possible is collated in a specific domain of interest, such as glaucoma-related information and/or images. Then, all the available data that is collated is labeled in a multi-label fashion, such as by using a label vector or the like. This labeled data may be referred to as a "universal" dataset, and this may be used to train a multi-label classifier, which may be machine learning model(s), that can classify the dataset into not just multi-class but also multi-label. In particular, an intuition in performing such data processing may be that the relevant features in the specific domain may be learned by this "universal" multi-label classifier. Such a classifier may then be used as a "pretrained" machine learning model(s)/network, such as a neural network, to classify other images within the same specific domain of interest. Based on such pretraining, the classifier may have already learned the necessary and/or key features in the domain of interest, and higher level features may be learned in a new smaller dataset.

Using such an approach in the glaucoma domain an excellent classification model, as described herein, is achieved for an overall glaucoma detection system. In particular, in various embodiments described herein, machine learning models/sub-models may be enhanced by using such a "domain-specific pre-training" approach. For example, sub-models such as disc hemorrhage, peripapillary atrophy, and vessel analysis models may be enhanced by using such an approach.

As one example, nearly 500 thousand eye fundus images from various sources, such as AREDS, UKBiobank, SiMES, Kaggle-DR, etc., were used in a massive multi-label classification machine learning model. In this example, the labels used were all fundus abnormality related diseases classes such as diabetic retinopathy (DR), age-related macular degeneration (AMD), etc. During pre-training, multiple labels, such as 15 labels, were used to create a large multi-label fundus dataset. Fundus abnormalities such as microaneurysms, vessel abnormalities, cotton-wool spots, and hemorrhages were learned by a machine learning model in the pre-training step. The model also learned to ignore common artefacts, insignificant retinal patterns, lighting variations, and/or anomalies.

FIG. 1 depicts the overall high-level architecture of the proposed pre-training technique 100. In various embodiments described herein, FIG. 1 shows a general technique 100 for the development and/or pre-training of machine learning model(s) for use in the glaucoma domain. In various embodiments, technique 100 may be referred to as the ODSP-DSPT algorithm. Feature vector generator 110 may accept as inputs, information regarding fundus images, such as from the database(s) described herein. Each image may include a label that identifies one or more eye conditions, such as any fundus abnormality related disease in the fundus image. For example, the fundus images that are received as input by feature vector generator 110 may include labels such as AMD, DR, glaucoma, and/or the like.

Using these input labels, feature vector generator 110 may generate one or more vectors for each image. For example, feature vector generator 110 may generate a multi-label vector that indicates the presence of and abnormality and/or other issue as seen in in an input fundus image using a value '1' and the absence of such an abnormality and/or other issue using a value '0'. This may be repeated for each label associated with each fundus image. Feature vector generator 110 may output one or more vectors, each associated with a fundus image, which include such binary values. The output of feature vector generator 110 may be input to a "universal" multi-label classifier 120. For example, feature vector generator 110 may accept 500 thousand fundus images each with 15 labels, as input, and may output a binary vector with 15 elements to multi-label classifier 120.

Multi-label classifier 120 may accept as input, one or more vectors from feature vector generator 110. Multi-label classifier 120 may use machine learning techniques to assign a single class label, out of several possible labels, to each vector that it receives from multi-label classifier 120. For example, multi-label classifier 120 may use a neural network, such as a deep neural network architecture, to classify and assign the single class label. The labels may be considered a "universal" label, which takes into account many possible eye conditions identified in fundus images. Thus, each fundus image input to feature vector generator 110 may have a "universal" label associated with it assigned by multi-label classifier 120. Multi-label classifier 120 may output the trained machine learning model and/or its properties, such as its weights, to optimized specific small data classifier 130. For example, multi-label classifier 120 may output a domain-specific, such a glaucoma-specific, pre-trained model and its properties to optimized specific small data classifier 130. This optimized specific small data classifier 130 may further process the input model that it receives, and it may generate a pre-trained machine learning model to be used by glaucoma screening system 200 and/or its constituent systems and processes.

Disc Hemorrhage Model (DHM)

In various embodiments described herein, machine learning model(s), such as a neural network that may be using a deep learning architecture, may be pre-trained with a dataset of eye fundus. In particular, the neural network may be pre-trained to detect one or more abnormalities in fundus images, for example, using datasets available to perform such pre-training. For example, this pre-training may include the use of general technique 100 for the development and/or pre-training of machine learning model(s) for use in the glaucoma domain. As one example, a deep machine learning architecture named "EfficientNet B5", was pre-trained with the "ImageNet" dataset. This dataset was implemented to train a neural network to detect the disc hemorrhages in fundus images. This dataset included 150 images with disc hemorrhages and 650 normal or without disc hemorrhages that were used to train and test the machine learning model.

The training dataset of eye fundus may first be processed, scaled, cropped, resized, transformed, and/or otherwise altered in order to reduce the number of retinal features encountered by the machine learning model(s). The sets of images within the dataset may be randomly or deterministically augmented, for example at each epoch, to produce variations in the dataset. For example, rotation, translation, and/or sheering with noise addition may be used to generate a new dataset containing such variations. During the training of the machine learning model(s), an early stopping mechanism for the training may be employed if no improvement in the error and/or training loss is observed in a predetermined number of epochs. In some instances, the stopping mechanisms may be employed if no improvement in the error and/or training loss is observed beyond a predetermined or dynamically changing threshold. The model(s) parameters with the least error and/or best training loss may be saved for future use. Another dataset may be used for validation and determination of accuracy of the trained machine learning model(s).

Continuing with the previous example of the neural network, "EfficientNet B5," full-color fundus images were first cropped using automated AI to get only the optic disc area of the retina. These images were then resized to 100×100 pixels. This cropping and resizing reduced the number of retinal features that the neural network encountered, given the relatively small amount of training data. The image sets were randomly augmented at each epoch for variation with rotation, translation and sheering with noise addition. This augmentation of the images resulted in newly generated images, which included up to 35 times the number of images as in the original number of images. An early stopping mechanism was employed wherein the training was stopped if no improvement in training loss is seen in 25 consecutive epochs. The network weights with the best training loss were saved. For external validation, another dataset obtained from the Department of Ophthalmology at Icahn School of Medicine at Mount Sinai was used. This validating dataset included 144 images with disc hemorrhage and 831 normal or without disc hemorrhages images. For detection of disc hemorrhage on the external validation dataset, 93.13% accuracy (95% CI: 91.35% to 94.64%) was achieved with a sensitivity of 71.53% (95% CI: 63.42% to 78.73%), a specificity of 96.87% (95% CI: 95.45% to 97.95%), and a kappa score of 0.71 (95% CI: 0.65 to 0.78).

Figure 2:
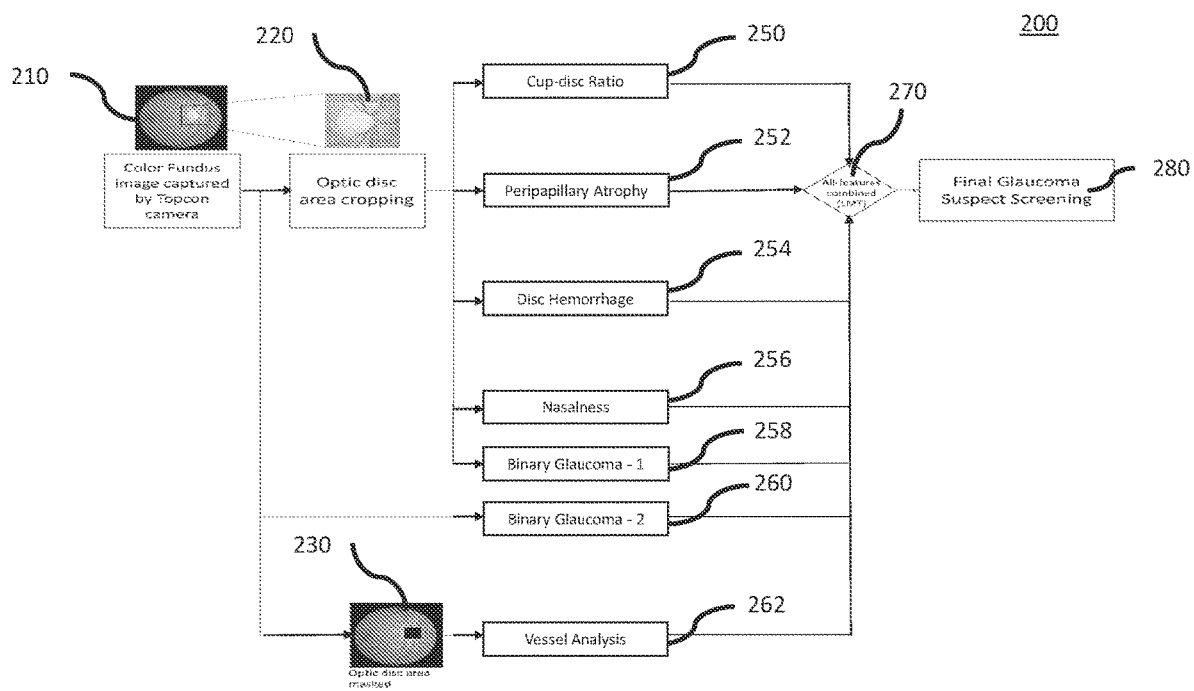
FIG. 2 depicts an example glaucoma screening system according to various embodiments of the present disclosure.

FIG. 2 depicts an example glaucoma screening system 200. This glaucoma screening system 200 is a solution made by iHealthscreen™. The system 200 may be used to screen individuals at risk of developing glaucoma and/or individuals at risk of having the disease worsening within them. The system 200 accepts as input eye fundus image, such as a fundus image for each eye of an individual. This input may be analyzed to automatically evaluate the features such as the cup-disc-ratio, the presence of peripapillary atrophy, disc hemorrhages, blood vessel pattern analysis, and/or the like. The system 200 may use machine learning model(s)/algorithm(s), such as deep neural network model(s), designed to evaluate a cumulative risk of glaucoma based on these features. The system 200 may them provide a final output, such as a binary output, indicating whether an individual is at risk of glaucoma or not, and/or to what extent the individual is at risk. As such, the system and its output may be used for glaucoma screening of an individual.

FIG. 2 shows a technical overview of the constituent parts of the glaucoma screening system 200. In general, as can be seen in FIG. 2, the system 200 combines multiple deep learning as well as traditional machine learning model(s) and approaches to build an accurate glaucoma screening system based on input fundus image(s). In particular, glaucoma screening system 200 of FIG. 2 includes a camera sensor 210, optic disc cropping system 220, image masking system 230, a cup-to-disc ratio estimation system 250, a peripapillary atrophy detection system 252, a disc hemorrhage detection system 254, nasalness system 256, a first binary classifier system 258, a second binary classifier system 260, a vessel analysis system 262, and a logistic model tree classifier 270, and a final glaucoma screening component 280.

Camera sensor 210 may be any suitable image and/or video capture device that may be able to capture fundus images from an individual. For example, camera sensor 210 may be fundus cameras available from Welch Allyn, Digisight, Volk, Topcon, Zeiss, Canon, Nidek, Kowa, CSO, CenterVue, Ezer, Optos and/or the like. Camera sensor 210 may capture fundus image(s) and may provide the image(s) to optic disc cropping system 220 and to image masking system 230.

Optic disc cropping system 220 may crop the fundus image(s) that it receives. Optic disc cropping module 220 may additionally or alternatively process, scale, resize, transform, and/or otherwise alter the image(s) that it receives. In various embodiments, optic disc cropping system 220 may reduce the number of retinal features in the fundus image(s) that it receives by performing one or more alterations to the image(s). This reduction in retinal features may be advantageous when the image(s) are processed by machine learning model(s), such as the machine learning model(s) used by the cup-to-disc ratio estimation system 250, the peripapillary atrophy detection system 252, the disc hemorrhage detection system 254, the nasalness system 256, the first binary classifier system 258, the second binary classifier system 260, the vessel analysis system 262, and/or the logistic model tree classifier 270.

Optic disc masking system 230 may mask the optic disc area in the fundus image(s) that it receives. For example, optic disc masking system 230 may mask the optic disc area that may be cropped by optic disc cropping system 220.

The cup-to-disc ratio estimation system 250 may take the retinal disc and/or macula center image or cropped disc center image(s) as input and returns the high cup-to-disc ratio probability or glaucoma probability and the binary value of the glaucoma subject or normal.

The peripapillary atrophy detection system 252 may take the retinal disc and/or macula center image or cropped disc center image as input and returns the probability of presence of peripapillary atrophy or the subject's glaucoma probability and the binary value of the glaucoma subject or normal.

The disc hemorrhage detection system 254 may take the retinal disc and/or macula center image or cropped disc center image as input and returns the probability of presence of disc hemorrhage probability and the subject's glaucoma probability and the binary value of the glaucoma subject or normal.

In various embodiments, each of the the cup-to-disc ratio estimation system 250, the peripapillary atrophy detection system 252, the disc hemorrhage detection system 254, and the nasalness system 256 may be pre-trained using the technique, such as the general technique 100 for the development and/or pre-training of machine learning model(s), described with reference to FIG. 1.

The nasalness system 256 may take the retinal disc and/or macula center image as input and returns the nasalness probability as output which is a significant risk factor for glaucoma.

The first binary classifier system 258 may take the retinal disc and/or macula center image as input and returns the glaucoma probability and binary value of the glaucoma subject or normal.

The second binary classifier system 260 may take the retinal disc and/or macula center image as input and returns the glaucoma probability without the disc area and binary value of the glaucoma subject or normal.

The vessel analysis system 262 may take the retinal disc and/or macula center image as input and returns the glaucoma probability without the disc area and binary value of the glaucoma subject or normal.

The logistic model tree (LMT) classifier 270 may receive the outputs of each of the each of the cup-to-disc ratio estimation system 250, the peripapillary atrophy detection system 252, the disc hemorrhage detection system 254, the nasalness system 256, the first binary classifier system 258, the second binary classifier system 260, and the vessel analysis system 262 and may combine these outputs to produce a probability/likelihood risk score of glaucoma. LMT considers one or multiple parameters through its function to determine the glaucoma or non-glaucoma. For example, logistic model tree (LMT) classifier 270 may be used to combine each of the risk scores that it receives as input to produce a probability/likelihood risk score of glaucoma. The LMT classifier 270 may output its result to final glaucoma screening component 280. Final glaucoma screening component 280 may make a determination of whether glaucoma is and/or will be present based on the probability/likelihood of glaucoma that it receives. Final glaucoma screening component 280 may also output the indications and/or risk scores associated with the cup-to-disc ratio estimation system 250, the peripapillary atrophy detection system 252, the disc hemorrhage detection system 254, the nasalness system 256, the first binary classifier system 258, the second binary classifier system 260, and/or the vessel analysis system 262. This output may be used to indicate the significance or risk associated with each of the associated abnormalities of the eyes.

Figure 3:
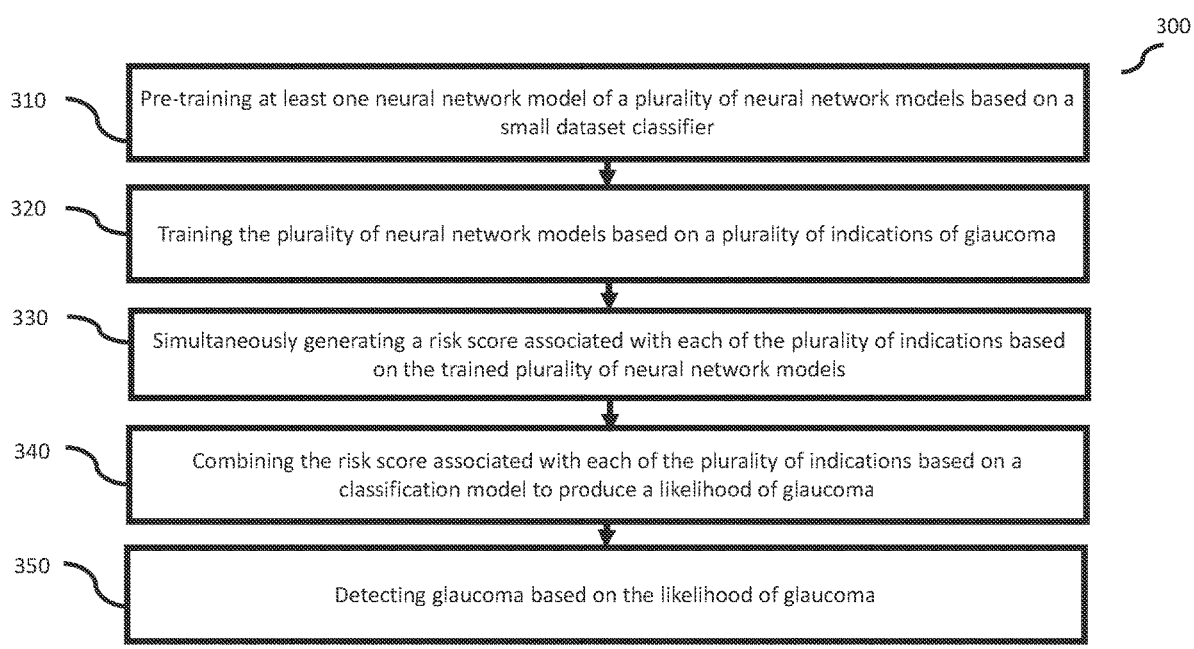
FIG. 3 is a flow diagram of an example process of detecting glaucoma according to various embodiments of the present disclosure.

FIG. 3 is a flow diagram of an example process of detecting glaucoma according to various embodiments of the present disclosure. At 310, at least one neural network model of a plurality of neural network models may be pre-trained using a small data classifier. At 320, the plurality of neural network models may be trained based on a plurality of indications of glaucoma. At 330, a risk score associated with each of the plurality of indications may be simultaneously generated based on the trained plurality of neural network models. At 340, the risk score associated with each of the plurality of indications may be combined based on a classification model to produce a likelihood of glaucoma. At 350, a determination of whether glaucoma is present may be made based on the likelihood of glaucoma. Based on the likelylihood or probability and the samples, a glaucoma and non-glaucoma or normal class is determined through a cutoff value.

EfficientNet Architecture for Individual Feature Based Glaucoma Risk Probability Generation The EfficientNet [1] architecture uses a model scaling technique for neural networks performing deep learning tasks. The EfficientNet architecture uses a simple yet highly effective compound coefficient to scale up convolutional neural networks (CNNs) in a more structured manner. Unlike conventional approaches that arbitrarily scale network dimensions, such as width, depth and resolution, this technique uniformly scales each dimension with a fixed set of scaling coefficients. The compound scaling technique used by EfficientNet is based by the intuition that if the input image is bigger, then the network needs more layers to increase the receptive field and more channels to capture more fine-grained patterns on the bigger image.

Any neural network architecture may be used with the methods and systems for predicting and detecting the onset of glaucoma described herein. For example, in addition to or instead of EfficentNet, the architectures associated with Inception, Resnet, Xception, and/or the like may be used. For these methods and systems, for the experiments described herein, a version of EfficientNet architecture known as "EfficientNetB4" was used. This architecture includes 19.5 million parameters, and a depth of 258 layers. Using the ImageNet dataset, the architecture achieved 82.9% accuracy (top-1) and 96.4% accuracy (top-5).

Through experimentations, such as what is describes in the examples below, it was determined that "EfficientNetB4" achieved efficient learning without the pitfalls of higher inference time, memory usage, and/or slower response times. After experimentation, as compared to the architectures used by Inception, Resnet and Xception, "EfficientNetB4" appeared to be the best architecture the prediction of glaucoma.

EXAMPLES

Data used as well as the experimental results as related to the models used by the methods, systems, and computer program products discussed herein are described in the Examples below. However, these Examples are only for illustrative purposes, and the data used as well as the experimental results as related to the present invention is not limited to the specific Examples mentioned below in any way.

Table 1 shows information regarding data from the UK Biobank. This data is also discussed in Appendix A included herein.

TABLE 1

| UK Biobank Data |
|---|
| Number of glaucoma patients (overall) - 9198 |
| Number of fundus images of glaucoma patients - 301 |
| Number of images whose CDR identified as 0.6 and above by the system - 127 |
| Number of images identified as 0.4 to 0.6 - 82 |
| Number of images below 0.4 - 92 |
| Number of images with peripapillary atrophy, as graded by the peripapillary identification system - 39 |
| Number of images with disc hemorrhages (identified with DR hemorrhage system) - 12 |

Example 1

Peripapillary Atrophy Experiments

Tables 2A and 2B show datasets used for peripapillary atrophy experiments and results of the peripapillary experiments respectively. Some of the datasets are also discussed in Appendix A included herein.

TABLE 2A

| Datasets Used for Peripapillary Atrophy Experiments |
|---|
| Datasets used - IDRID, ORIGA-light and REFUGE |
| Training dataset |
| Number of positive images - 294 |
| Number of negative images (no pp atrophy) - 600 (randomly selected) |
| Test |
| Number of positive images - 42 |
| Number of normal images - 42 |

TABLE 2B

Results of Peripapillary Atrophy Experiments

| Statistic | Value | 95% CI |
|---|---|---|
| Sensitivity | 93.18% | 81.34% to 98.57% |
| Specificity | 97.67% | 87.71% to 99.94% |
| Positive Predictive Value | 97.62% | 85.51% to 99.65% |
| Negative Predictive Value | 93.33% | 82.43% to 97.66% |
| Accuracy | 95.40% | 88.64% to 98.73% |

From the prospective trial data, using the peripapillary atrophy model described herein, there were 43 images classified as images with peripapillary atrophy. The images were saved separately.

Example 2

Results on CDR

Table 3A shows the results of CDR experiments. Tables 3B and 3C show validation results from mixed datasets as well as external datasets, respectively. Table 3D shows sensitivity and specificity for CDR values of 0.6 and above. Some of the datasets are also discussed in Appendix A included herein. The model described herein categorizes the images in 3 classes—CDR values below 0.4, CDR values between 0.4 and 0.6, and CDR values 0.6 and above. While the training dataset was built using AREDS, ORIGA-light and REFUGE, the experimental results shown here are from the prospective trial.

TABLE 3A

CDR Results

Training dataset (mixed group)

CDR < 0.4-1000
0.4 < CDR < 0.6-390
0.6 < CDR - 600

TABLE 3B

CDR Validation results from the mixed dataset (AREDS, ORIGA-light & REFUGE)

| Actual | Predicted CDR < 0.4 | Predicted 0.4 < CDR < 0.6 | Predicted 0.6 < CDR |
|---|---|---|---|
| CDR < 0.4 | 34 | 3 | 4 |
| 0.4 < CDR < 0.6 | 3 | 24 | 1 |
| 0.6 < CDR | 4 | 6 | 72 |

Weighted Kappa = 0.785
Kappa = 0.772
SE of kappa = 0.046
95% confidence interval: From 0.682 to 0.861

TABLE 3C

CDR External validation results (from the prospective trial)

| Actual | Predicted CDR < 0.4 | Predicted 0.4 < CDR < 0.6 | Predicted 0.6 < CDR |
|---|---|---|---|
| CDR < 0.4 | 88 | 19 | 6 |
| 0.4 < CDR < 0.6 | 2 | 66 | 22 |
| 0.6 < CDR | 8 | 13 | 101 |

Weighted Kappa = 0.717
Kappa = 0.675

TABLE 3C-continued

CDR External validation results (from the prospective trial)

| Actual | Predicted CDR < 0.4 | Predicted 0.4 < CDR < 0.6 | Predicted 0.6 < CDR |
|---|---|---|---|

SE of kappa = 0.034
95% confidence interval: From 0.608 to 0.742

TABLE 3D

Sensitivity and Specificity for CDR 0.6 and above

| Statistic | Value | 95% CI |
|---|---|---|
| Sensitivity | 82.79% | 74.90% to 89.02% |
| Specificity | 86.21% | 80.69% to 90.63% |
| Positive Predictive Value | 78.29% | 71.70% to 83.70% |
| Negative Predictive Value | 89.29% | 84.91% to 92.51% |
| Accuracy | 84.92% | 80.56% to 88.63% |

Example 3

Disc Hemorrhage Experiments

Tables 4A shows the training data for disc hemorrhage experiments. Tables 4B and 4C show the confusion matrix used for the disc hemorrhage experiments and the results of these experiments, respectively. Table 4D and 4E show the confusion matrix used for an external dataset used in disc hemorrhage experiments and the results of these experiments.

TABLE 4A

Training data for Disc Hemorrhage Experiments

Total positive images — 287 (from AREDS, SiMES, UK Biobank and other public sources)
Total negative (no disc hemorrhages) — 860 images (randomly chosen from the same sources)

TABLE 4B

Confusion Matrix (with test data for model building) for Disc Hemorrhage Experiments

| | Disc Hem present (predicted) | Disc hem absent (predicted) |
|---|---|---|
| Disc hem present | 73 | 13 |
| Disc Hem absent | 33 | 225 |

TABLE 4C

Results for Disc Hemorrhage Experiments

| Statistic | Value | 95% CI |
|---|---|---|
| Sensitivity | 84.88% | 75.54% to 91.70% |
| Specificity | 87.21% | 82.51% to 91.03% |
| Positive Predictive Value | 68.87% | 61.37% to 75.49% |
| Negative Predictive Value | 94.54% | 91.28% to 96.62% |
| Accuracy | 86.63% | 82.57% to 90.04% |

TABLE 4D

Confusion Matrix (on External Dataset) for Disc Hemorrhage Experiments

|  | Disc Hem present (predicted) | Disc hem absent (predicted) |
| --- | --- | --- |
| Disc hem present | 119 | 25 |
| Disc Hem absent | 62 | 769 |

TABLE 4E

Results of External Dataset for Disc Hemorrhage Experiments

| Statistic | Value | 95% CI |
| --- | --- | --- |
| Sensitivity | 82.64% | 75.45% to 88.44% |
| Specificity | 92.54% | 90.54% to 94.23% |
| Positive Predictive Value | 65.75% | 59.90% to 71.15% |
| Negative Predictive Value | 96.85% | 95.56% to 97.78% |
| Accuracy | 91.08% | 89.11% to 92.79% |

Example 4

Glaucoma Vs Non-Glaucoma Model Results on UK Biobank Data

Table 5 shows the experimental results of the glaucoma model described herein versus a non-glaucoma model as related to the UK Biobank data. The UK Biobank data is also discussed in Appendix A included herein.

TABLE 5

Results of Glaucoma Vs Non-Glaucoma Model on UK Biobank Data

| Statistic | Value | 95% CI |
| --- | --- | --- |
| Sensitivity | 85.00% | 70.16% to 94.29% |
| Specificity | 87.00% | 78.80% to 92.89% |
| Positive Predictive Value | 72.34% | 60.78% to 81.53% |
| Negative Predictive Value | 93.55% | 87.35% to 96.82% |
| Accuracy | 86.43% | 79.62% to 91.63% |

Example 5

Glaucoma Vs Non-Glaucoma Model Results on Origa Data

Table 6 shows theexperimental results of the glaucoma model described herein versus a non-glaucoma model as related to the ORIGA-light data. The ORIGA-light data is also discussed in Appendix A included herein.

TABLE 6

Results of Glaucoma Vs Non-Glaucoma Model on ORIGA-light Data

| Statistic | Value | 95% CI |
| --- | --- | --- |
| Sensitivity | 89.26% | 83.15% to 93.74% |
| Specificity | 93.81% | 91.33% to 95.76% |
| Positive Predictive Value | 81.10% | 75.23% to 85.84% |
| Negative Predictive Value | 96.71% | 94.87% to 97.90% |
| Accuracy | 92.77% | 90.50% to 94.64% |

Example 6

All Features Results on UK Biobank Data

Figure 4:
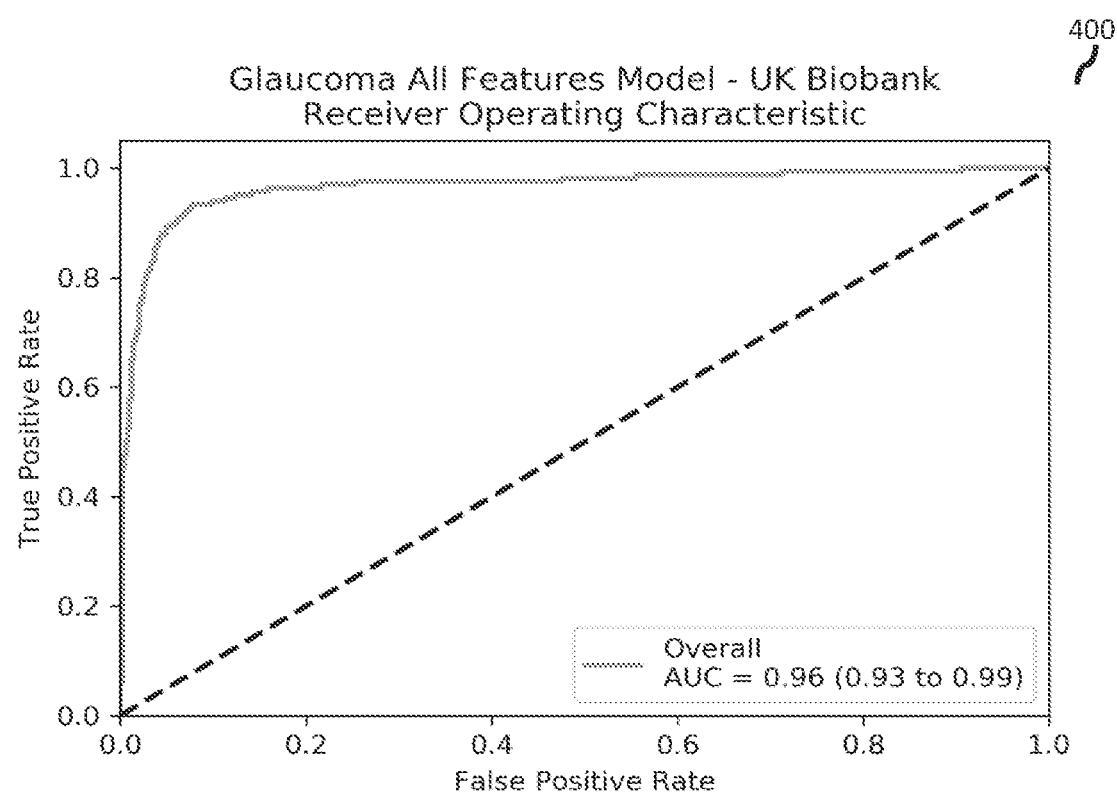
FIG. 4 depicts a graph related to the results of the all features experiments as related to UK Biobank data in terms the true positive rate versus the false positive rate according to various embodiments of the present disclosure.

Table 7 shows the experimental results of all features described herein as related to the UK Biobank data. FIG. 4 depicts a graph related to the results of the all features experiments as related to the UK Biobank data in terms the true positive rate versus the false positive rate. The UK Biobank data is also discussed in Appendix A included herein.

TABLE 7

Results of All Features Experiment on UK Biobank Data

| Statistic | Value | 95% CI |
| --- | --- | --- |
| Sensitivity | 95.00% | 83.08% to 99.39% |
| Specificity | 94.00% | 87.40% to 97.77% |
| Positive Predictive Value | 86.36% | 74.40% to 93.24% |
| Negative Predictive Value | 97.92% | 92.40% to 99.45% |
| Accuracy | 94.29% | 89.05% to 97.50 |

Example 7

All Features Results on Origa-light Data

Figure 5:
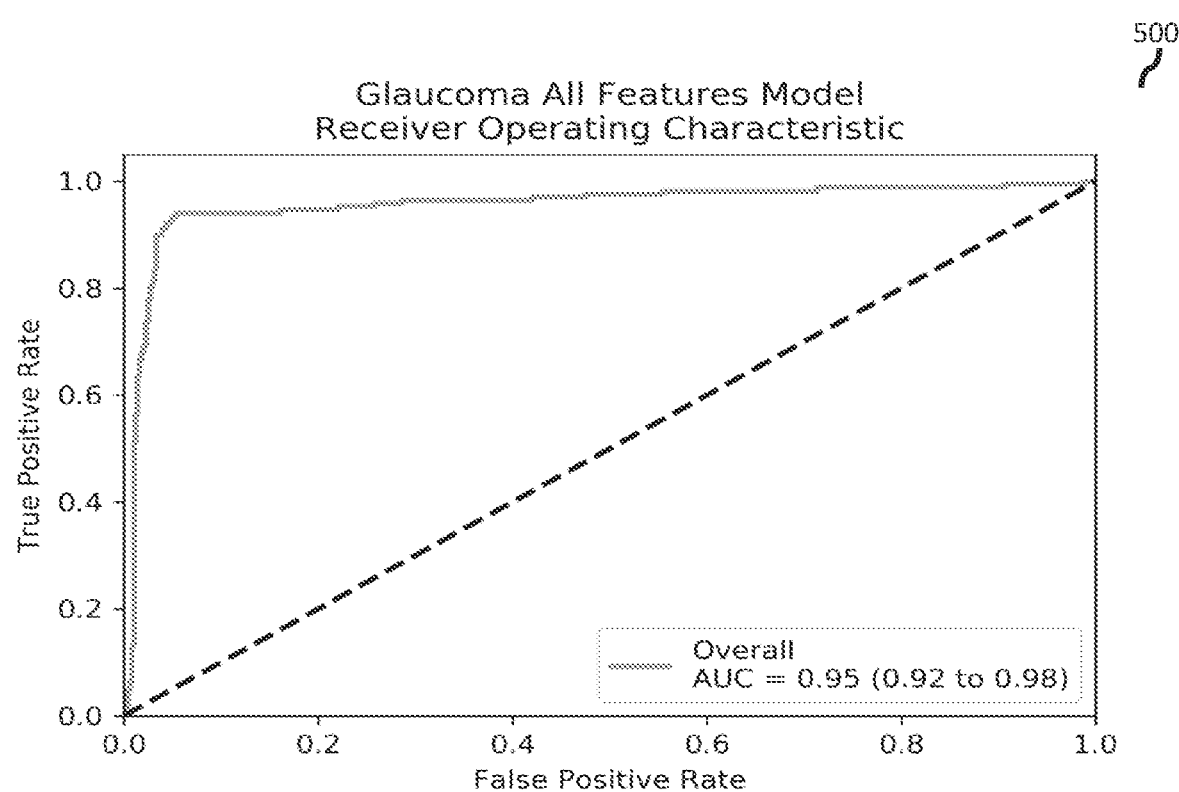
FIG. 5 depicts a graph related to the results of the all features experiments as related to ORIGA-light data in terms the true positive rate versus the false positive rate according to various embodiments of the present disclosure.

Table 8A shows the data split of all features described herein as related to the ORIGA-light data. Table 8B shows the predicted experimental results of all features described herein as related to the color fundus image taken from ORIGA-light data. Table 8C shows the experimental results of all features described herein as related to the ORIGA-light data. FIG. 5 depicts a graph related to the results of the all features experiments as related to the color fundus image based glaucoma detection taken from the ORIGA-light data in terms the true positive rate versus the false positive rate. The ORIGA-light data is also discussed in Appendix A included herein.

TABLE 8A

Data Split All Features Experiment on ORIGA-light Data

Data split -

Total: 648
Glaucoma: 167
No-glaucoma: 481

TABLE 8B

Predicted Results of All Features Experiment on ORIGA-light Data

|  | Glaucoma (predicted) | No glaucoma (predicted) |
| --- | --- | --- |
| Glaucoma | 156 | 11 |
| No glaucoma | 27 | 454 |

TABLE 8C

Results of All Features Experiment on ORIGA-light Data

| Statistic | Value | 95% CI |
| --- | --- | --- |
| Sensitivity | 93.41% | 88.52% to 96.67% |
| Specificity | 94.39% | 91.94% to 96.27% |
| Positive Predictive Value | 85.25% | 79.98% to 89.31% |
| Negative Predictive Value | 97.63% | 95.89% to 98.65% |
| Accuracy | 94.14% | 92.04% to 95.82% |

Appendix a: Data Sources

UK Biobank

UK Biobank [2] has involved the collection of extensive baseline questionnaire data, physical measurements and biological samples from 500,000 men and women aged 40-69 at baseline between 2006 and 2010 in 22 centers across the UK. In the on-going study, it re-contacted subjects to the follow up information. Out of this large and popular dataset, subjects who had the follow up data were chosen.

This large open access database has enabled large studies on socio-demographic and epidemiological associations for an extensive range of health-related outcomes and conditions. Ocular data collection in UK Biobank commenced in September 2009. Acquisition of OCT images and retinal photography began in December 2009. The methods and protocol for the ocular examination component of UK Biobank were designed by ophthalmologists from Moorfields Eye Hospital, London, UK. Written, informed consent was obtained for all participants in UK Biobank. OCT images were acquired using Spectral Domain OCT device (3D OCT-1000 Mark II). This system has an axial resolution of 6 µm and an image acquisition speed of 18,000 A-scans per second (each A-scan is the measurement of the reflectance profile along the optical axis within the retina). OCT images were obtained using a raster scan protocol, 6 mm×6 mm in area, centered on the fovea. This raster scan consisted of 128 B-scans, each composed of 512 A-scans (a B-scan is a two-dimensional, cross-sectional image of retinal tissue). Using this protocol, a whole macular 3D volume of 512 A-scans by 128 B-scans is obtained in 3.6 seconds (512*128/18000).

Age-Related Eye Disease Study (AREDS)

AREDS is a major clinical trial sponsored by the National Eye Institute. AREDS participants were 55 to 80 years old at enrollment, and they had to be free of any illness or condition that would make a long-term follow-up or compliance with study medications unlikely. Based on fundus photographs graded by a central reading center, the best-corrected visual acuity, and ophthalmologic evaluations, 4,753 participants were enrolled in one of several AMD categories, including persons with no AMD. Subjects were randomly assigned to the vitamins and mineral supplements and placebo groups.

AREDS participants were assigned to four categories based on the size and extent of drusen and other AMD lesions: Normal, Early, Intermediate, and Advanced or Late AMD. These assignments were made for the left and right eyes individually. Deidentified AREDS data was used in this study and was approved by the National Eye Institute Data Access Committee, National Institute of Health.

ImageNet

Pre-trained networks helped greatly when dealing with smaller datasets. The efficientNetB4 architecture used in this experiment pretrained on the popular ImageNet dataset. The ImageNet [3] project is a large visual database designed for use in visual object recognition software research. The subset of ImageNet used for pretraining the architecture has more than 1 million images with 1000 categories. These images have been hand-annotated for the classes and categories by the project.

Refuge

REFUGE dataset part of one of the first open challenges focused on glaucoma classification and optic disc/cup segmentation from color fundus photographs. The challenge consisted of two primary tasks, namely optic disc/cup segmentation and glaucoma classification. As part of REFUGE, the dataset is publicly released including 1200 fundus images with ground truth segmentations and clinical glaucoma labels.

ORIGA-Light

The ORIGA-light dataset [4] is an ophthalmic reference image database specifically designed for glaucoma analysis. ORIGA-light serves as a benchmarking resource for researchers to evaluate image processing algorithms that detect and analyze various image signs highly related to glaucoma diagnosis. To facilitate this, the authors of ORIGA used their in-house grading tools to grade several glaucoma-related signs. The publicly available dataset that we used has 650 graded images, out of which 460 are healthy and the rest are graded as glaucoma, taken from adults aged between 40 and 80 years. Each image is segmented and annotated by trained professionals from the Singapore Eye Research Institute.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other elements, steps, methods, and techniques that are insubstantially different from those described above and/or in the appended claims are also intended to be within the scope of the disclosure.

REFERENCES

[1] M. Tan and Q. V. Le, "Efficientnet: Rethinking model scaling for convolutional neural networks," *arXiv preprint arXiv:* 1905.11946, 2019.

[2] C. Sudlow et al., "UK biobank: an open access resource for identifying the causes of a wide range of complex diseases of middle and old age," *PLoS medicine*, vol. 12, no. 3, p. e1001779, 2015.

[3] J. Deng, W. Dong, R. Socher, L.-J. Li, K. Li, and L. Fei-Fei, "Imagenet: A large-scale hierarchical image database," in 2009 *IEEE conference on computer vision and pattern recognition*, 2009: Ieee, pp. 248-255.

[4] Z. Zhang et al., "Origa-light: An online retinal fundus image database for glaucoma analysis and research," in 2010 *Annual International Conference of the IEEE Engineering in Medicine and Biology*, 2010: IEEE, pp. 3065-3068.

What is claimed is:

1. A method of detecting glaucoma, the method comprising:
   obtaining a first dataset including eye images;
   augmenting the eye images to generate a second dataset including eye image variations by at least one of rotation, translating, or sheering the eye images;
   pre-training at least one neural network model of a plurality of neural network models based on a small data classifier, wherein the pre-training is performed using the second dataset and includes:
      generating a plurality of vectors based on the eye image variations, wherein each vector includes a plurality of labels with binary values designating eye conditions;
      assigning a class label to each vector based on the plurality of labels; and
      generating a glaucoma-specific pre-trained model based on the assigned class labels;

training the plurality of neural network models based on a plurality of indications of glaucoma based on retinal data including at least two of a peripapillary atrophy value, a disc hemorrhage value, and a blood vessel structure analysis value;

simultaneously generating a risk score associated with each of the plurality of indications based on the trained plurality of neural network models;

combining the risk score associated with each of the plurality of indications based on a classification model to produce a likelihood of glaucoma; and determining whether glaucoma is present based on the likelihood of glaucoma.

2. The method of claim 1, wherein the plurality of neural network models are each a deep learning neural network model.

3. The method of claim 1, wherein the plurality of indications of glaucoma further include at least two of a cup-disk ratio, a nasalness value, and a retinal entire image value.

4. The method of claim 1, wherein the risk score associated with each of the plurality of indications includes at least one continuous probability value.

5. The method of claim 4, wherein the plurality of indications includes a cup-disk ratio, and wherein the risk score associated with the cup-disk ratio includes at least two continuous probability values.

6. The method of claim 1, wherein the classification model is a logistic model tree (LMT).

7. The method of claim 1, further comprising displaying, on a display, the determination of whether glaucoma is present, the plurality of indications, and the risk score associated with each of the plurality of indications.

8. A system comprising:
a computing node comprising a computer readable storage medium having program instructions embodied therewith, the program instructions executable by a processor of the computing node to cause the processor to perform a method comprising:
obtaining a first dataset including eye images;
augmenting the eye images to generate a second dataset including eye image variations by at least one of rotation, translating, or sheering the eye images;
pre-training at least one neural network model of a plurality of neural network models based on a small data classifier, wherein the pre-training is performed using the second dataset and includes:
generating a plurality of vectors based on the eye image variations, wherein each vector includes a plurality of labels with binary values designating eye conditions;
assigning a class label to each vector based on the plurality of labels; and
generating a glaucoma-specific pre-trained model based on the assigned class labels;
training the plurality of neural network models based on a plurality of indications of glaucoma based on retinal data including at least two of a peripapillary atrophy value, a disc hemorrhage value, and a blood vessel structure analysis value;
simultaneously generating a risk score associated with each of the plurality of indications based on the trained plurality of neural network models;
combining the risk score associated with each of the plurality of indications based on a classification model to produce a likelihood of glaucoma; and
determining whether glaucoma is present based on the likelihood of glaucoma.

9. The system of claim 8, wherein the plurality of neural network models are each a deep learning neural network model.

10. The system of claim 8, wherein the plurality of indications of glaucoma further include at least two of a cup-disk ratio, a nasalness value, and a retinal entire image value.

11. The system of claim 8, wherein the risk score associated with each of the plurality of indications includes at least one continuous probability value.

12. The system of claim 11, wherein the plurality of indications includes a cup-disk ratio, and wherein the risk score associated with the cup-disk ratio includes at least two continuous probability values.

13. The system of claim 8, wherein the classification model is a logistic model tree (LMT).

14. The system of claim 8, wherein the method further comprises displaying, on a display, the determination of whether glaucoma is present, the plurality of indications, and the risk score associated with each of the plurality of indications.

15. A non-transitory computer-readable medium storing instructions that, when executed by a processor, cause the processor to perform a method for backing up and restoring a cluster of nodes, the method comprising:
obtaining a first dataset including eye images;
augmenting the eye images to generate a second dataset including eye image variations by at least one of rotation, translating, or sheering the eye images;
pre-training at least one neural network model of a plurality of neural network models based on a small data classifier, wherein the pre-training is performed using the second dataset and includes:
generating a plurality of vectors based on the eye image variations, wherein each vector includes a plurality of labels with binary values designating eye conditions;
assigning a class label to each vector based on the plurality of labels; and
generating a glaucoma-specific pre-trained model based on the assigned class labels;
training the plurality of neural network models based on a plurality of indications of glaucoma based on retinal data including at least two of a peripapillary atrophy value, a disc hemorrhage value, and a blood vessel structure analysis value;
simultaneously generating a risk score associated with each of the plurality of indications based on the trained plurality of neural network models;
combining the risk score associated with each of the plurality of indications based on a classification model to produce a likelihood of glaucoma; and
determining whether glaucoma is present based on the likelihood of glaucoma.

16. The non-transitory computer-readable medium of claim 15, wherein the plurality of neural network models are each a deep learning neural network model.

17. The non-transitory computer-readable medium of claim 15, wherein the plurality of indications of glaucoma further include at least two of a cup-disk ratio, a nasalness value, and a retinal entire image value.

18. The non-transitory computer-readable medium of claim 15, wherein the risk score associated with each of the plurality of indications includes at least one continuous probability value.

19. The non-transitory computer-readable medium of claim 15, wherein the plurality of indications includes a cup-disk ratio, and wherein the risk score associated with the cup-disk ratio includes at least two continuous probability values.

20. The non-transitory computer-readable medium of claim 15, wherein the classification model is a logistic model tree (LMT).

\* \* \* \* \*